US00PP08364P

United States Patent [19]

VandenBerg

[11] Patent Number: Plant 8,364

[45] Date of Patent: Sep. 7, 1993

[54] CHRYSANTHEMUM PLANT NAMED YELLOW DIAMOND

[75] Inventor: Cornelis P. VandenBerg, Salinas, Calif.

[73] Assignee: Yoder Brothers, Inc., Barberton, Ohio

[21] Appl. No.: 822,714

[22] Filed: Jan. 21, 1992

[51] Int. Cl.[5] ..... A01H 5/00

[52] U.S. Cl. ..... Plt./78

[58] Field of Search ..... Plt./78

[56] References Cited

U.S. PATENT DOCUMENTS 4,616,099 10/1986 Sparkes ..... 47/58

OTHER PUBLICATIONS

Chan, 1966, "Chrysanthemum and rose mutations induced by X-rays", Am. Soc. Hart. Sci. Proc., pp. 613-620.

Broertjes, 1966, "Mutation breeding of Chrysanthemums", Euphytica, 15:156-162.

Dowrick et al., 1966, "The induction of mutations in Chrysanthemum using X- and gamma radiaton", Euphytica, 15:204-210.

Broertjes et al., 1980, "A mutant of a mutant of a mutant of a . . . Irradiation of progressive radiation-induced mutants in a mutation breeding programme with *Chrysanthemum morifolim*", *Euphtica 29:525-530.*

Gosling, ed., 1979, "The Chrysanthemum Manual-" 6th edition. The National Chrysanthemum Society, London, Essex Telegraph Press, Ltd., pp. 329-336.

Broertjes et al. 1978, "Application of Mutation Breeding Methods in the Improvement of Vegetatively Propagated Crops", Elsevier Sci. Pub. Co., New York, pp. 162-175.

Searle, et al. 1968, "Chrysanthemums the Year Round", Blanford Press, London, pp. 27-29, 320-327.

*Primary Examiner*—Howard J. Locker

*Attorney, Agent, or Firm*—Foley & Lardner

[57] ABSTRACT

A Chrysanthemum plant named Yellow Diamond particularly characterized by its flat capitulum form; decorative capitulum type; yellow ray floret color; diameter across face of capitulum of 127 to 139 mm when fully opened, when grown as a pinched disbudded pot mum; photoperiodic flowering response to short days of 53 to 57 days; plant height, with 16 long days after sticking unrooted cuttings, and with 1 application of 2500 ppm B-9 SP, ranges from 18 to 25 cm when grown as a pinched pot mum with 4 cuttings in a 15 cm pot; spreading branching pattern, with each plant having 5 to 6 laterals after pinch, and its recommended grown as a disbud pot mum.

1 Drawing Sheet

The present invention comprises a new and distinct cultivar of Chrysanthemum, botanically known as *Dendranthema grandiflora*, and referred to by the cultivar name Yellow Diamond.

Yellow Diamond, identified as 5800 (85-789F02), is a product of a mutation induction program. The new cultivar was discovered and selected by Cornelis P. VandenBerg on Nov. 18, 1990 in a controlled environment in Salinas, Calif., as one flowering plant within a flowering block established as rooted cuttings from stock plants which had been exposed as unrooted cuttings to an X-ray source of 2000 rads in Fort Myers, Fla., on May 31, 1990. The irradiated parent cultivar, identified as 5194 (85-789B02), was a selection from an earlier mutation breeding program, in which the grandparent, an unnamed seedling, identified as 4149 (85-789002) was irradiated to intensify and possibly change the color of this unnamed seedling. The grandparent seedling 4149 (85-789002) is described as a flat decorative disbud pot mum with a very light pink ray floret color, a flowering response period of 54 to 62 days after start of short days, a plant height of 23 to 30 cm with one application of 2500 ppm B-9 SP, a spreading branching habit with 5 to 6 laterals after pinch and a diameter of capitulum of 127 to 155 mm when fully opened. This cultivar was discovered and selected as one flowering plant in August 1985 by Cornelis P. VandenBerg from the progeny of a cross made in 1984. The female parent was the cultivar identified as Charm, a pink flat decorative disbud pot mum, disclosed in U.S. Plant Pat. No. 5,502. The male parent was an unnamed seedling, identified as 0668 (82-051014) and described as a yellow flat daisy disbud pot mum with many ray florets.

The irradiation program resulting in Yellow Diamond had as its primary objective the expansion of color ranges of the unnamed grandparent cultivar. The grandparent cultivar had a very light pink ray floret color, which color as regarded as not commercially acceptable. Because all other traits of this cultivar were outstanding, an attempt was made to obtain different ray floret colors, while maintaining all other traits of the grandparent cultivar. The irradiation program comprised irradiating cuttings of the grandparent cultivar 4149 (85-789002) at irradiation levels of 1500, 1750 and 2000 rads. A total of 1264 cuttings harvested from a total of 225 irradiated plants were planted on November 9 and November 30. Of these, 24 initial selections were made, which selections were then revegetated and reflowered. Four consecutive flowerings resulted in discarding 19 of the original 24 selections on Nov. 9, 1988. Four selections were retained and one selection, identified as 6927, was reselected under code 5194 (85-789B02) as possible introduction, to be further tested in flowering programs in Salinas, Calif., and in Leamington, Ontario, Canada. These flowerings resulted in discarding three out of the five selections on Apr. 26, 1990, on Jul. 10, 1990, and on Dec. 7, 1990, and the decision to commercially introduce one remaining selection as White Diamond. White Diamond was commercially introduced in April 1991, and is disclosed in U.S. Plant Pat. No. 8,059. The one other remaining selection, 5194, with yellow ray floret color, was exhibiting bronze overtones, and the decision was made to irradiate 5194, with the object to obtain a clear yellow ray floret color, without the bronze overtones.

The irradiation program comprised irradiating cuttings of the parent cultivar 5194 (85-789B02) at irradiation levels of 1500, 1750 and 2000 rads. A total of 1265 cuttings harvested from a total of 225 irradiated plants were planted on Sep. 17 and Sep. 14, 1990. Of these, 16 initial selections were made, which selections were then revegetated and reflowered. Four consecutive flowerings resulted in discarding 13 of the original 16 selections on Aug. 19, 1991. Three selections were retained to be further tested in our Salinas, Calif., flowering programs. These flowerings resulted in the decision to commercially introduce one remaining selection as Yellow Diamond, because of the clear yellow ray floret color with no bronze overtones. The two other remaining selections were maintained to be further tested in low light winter flowerings in comparison with Yellow Diamond.

The first act of asexual reproduction of Yellow Diamond was accomplished when vegetative cuttings were taken from the initial selection in January 1991 in a controlled environment in Salinas, Calif., by technicians working under supervision of Cornelis P. VandenBerg.

Horticultural examination of controlled flowerings of successive plantings has shown that the unique combination of characteristics as herein disclosed for Yellow Diamond are firmly fixed and are retained through successive generations of asexual reproduction.

Yellow Diamond has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., under greenhouse conditions which approximate those generally used in commercial greenhouse practice.

The following traits have been repeatedly observed and are determined to be basic characteristics of Yellow Diamond, which, in combination, distinguish this Chrysanthemum as a new and distinct cultivar:

1. Flat capitulum form.
2. Decorative capitulum type.
3. Yellow ray floret color.
4. Diameter across face of capitulum of 127 to 139 mm when fully opened, when grown as a pinched disbudded pot mum.
5. Photoperiodic flowering response to short days of 53 to 57 days.
6. Plant height, with 16 long days after sticking unrooted cuttings, and with 1 application of 2500 ppm B-9 SP, ranges from 18 to 25 cm when grown as a pinched pot mum with 4 cuttings in a 15 cm pot.
7. Branching pattern is spreading, each plant having 5 to 6 laterals after pinch.
8. Recommended as disbud pot mum.

The accompanying photographic drawing is a color photograph of Yellow Diamond grown as a pinched disbudded pot mum with 4 cuttings in a 15 cm pot, with the colors being as nearly true as possible with illustrations of this type.

Of the commercial cultivars known to the inventor, the most similar in comparison to Yellow Diamond is the cultivar identified as White Diamond, disclosed in U.S. Plant Pat. No. 8,059. All traits of Yellow Diamond are similar to those of White Diamond except for ray floret color, diameter of capitulum, flower form and flowering response to short days. White Diamond has a white ray floret color with a cream center of the flower, while Yellow Diamond has a clear yellow ray floret color. The diameter of capitulum of Yellow Diamond is 6 to 20 mm smaller than the diameter of White Diamond. White Diamond has a very flat and formal flower form, while the flower form of Yellow Diamond is less formal and slightly reflexing when fully open. When grown side by side, Yellow Diamond is one to three days slower in flowering response to short days than White Diamond.

In the following description color references are made to The Royal Horticultural Society Colour Chart. The color values were determined on plant material grown as a pinched disbudded pot mum in Salinas, Calif., on Aug. 19, 1991.

Classification:

*Botanical.*—*Dendranthema grandiflora* cv Yellow Diamond.

*Commercial.*—Flat decorative disbud pot mum.

INFLORESCENCE

A. Capitulum:

*Form.*—Flat.

*Type.*—Decorative.

*Diameter across face.*—127 to 139 mm when fully opened.

B. Corolla of ray florets:

*Color (general tonality from a distance of three meters).*—Yellow.

*Color (upper surface).*—7A to 7C.

*Color (under surface).*—7B.

*Shape.*—Straight, cross section concave.

C. Corolla of disc florets:

*Color (mature).*—13B to 14B.

*Color (immature).*—144B to 144C.

D. Reproductive organs:

*Androecium.*—Present on disc florets only; very few disc florets, no pollen.

*Gynoecium.*—Present on both ray and disc florets.

PLANT

A. General appearance:

*Height.*—18 to 25 cm when grown as a pinched pot mum with 16 long days prior to start of short days, with 1 application of 2500 ppm B-9 SP.

*Branching pattern.*—Spreading and prolific, with 5 to 6 laterals after pinch.

B. Foliage:

*Color (upper surface).*—147A.

*Color (under surface).*—147B.

I claim:

1. A new and distinct Chrysanthemum plant named Yellow Diamond, as described and illustrated.

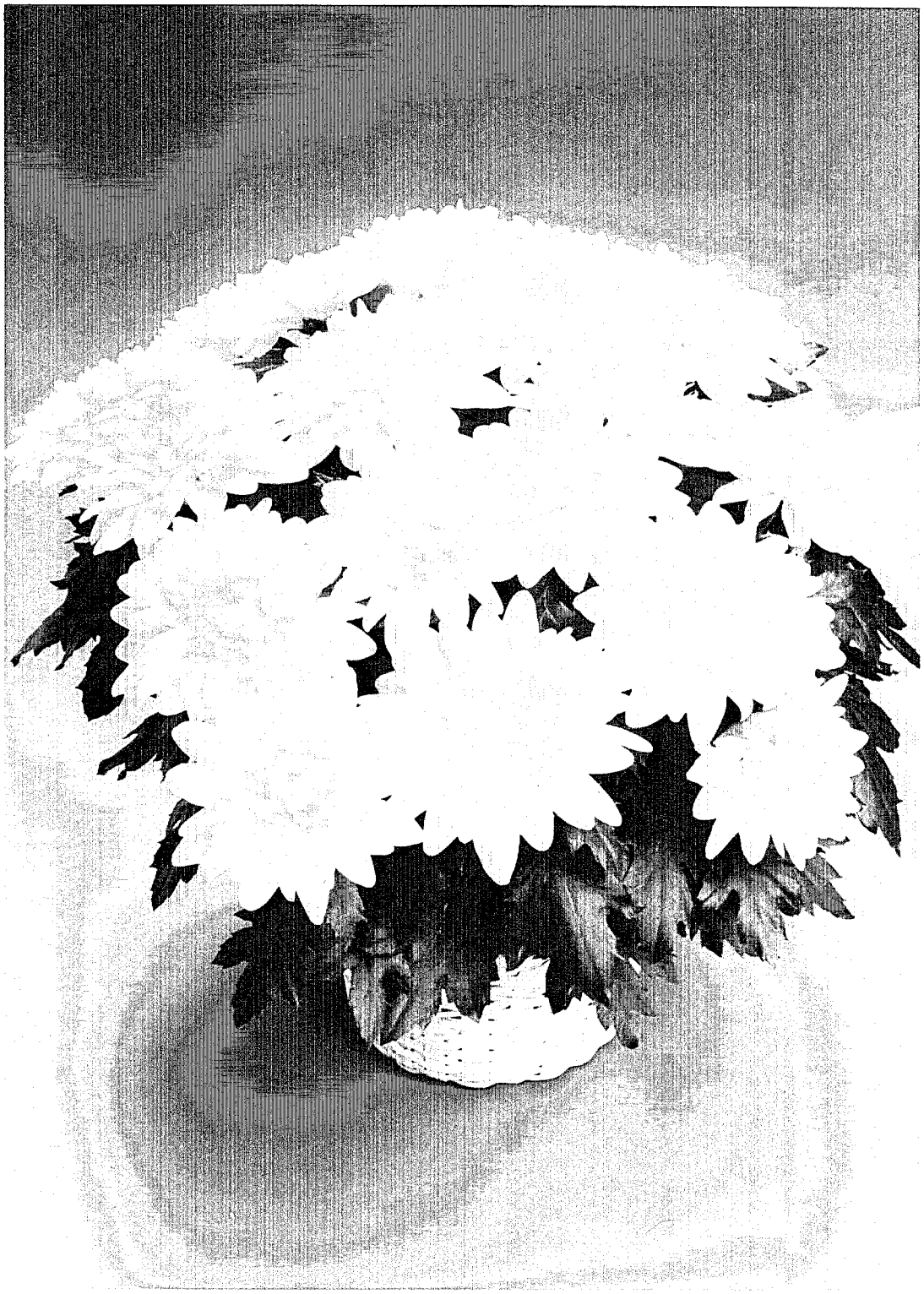

* * * * *